United States Patent
Ali et al.

(10) Patent No.: US 12,350,146 B2
(45) Date of Patent: Jul. 8, 2025

(54) PROSTHETIC HEART VALVE WITH A DIHEDRAL GUARD MECHANISM

(71) Applicants: Fayzan Ali, Saint Louis, MO (US); Rayan Ali, Saint Louis, MO (US)

(72) Inventors: Fayzan Ali, Saint Louis, MO (US); Rayan Ali, Saint Louis, MO (US)

(73) Assignee: Fayzan Ali, Saint Louis, MO (US)

( * ) Notice: Subject to any disclaimer, the term of this patent is extended or adjusted under 35 U.S.C. 154(b) by 508 days.

(21) Appl. No.: 17/893,032

(22) Filed: Aug. 22, 2022

(65) Prior Publication Data
US 2024/0058117 A1 Feb. 22, 2024

(51) Int. Cl.
*A61F 2/24* (2006.01)

(52) U.S. Cl.
CPC .... *A61F 2/2403* (2013.01); *A61F 2230/0054* (2013.01)

(58) Field of Classification Search
CPC .............................. A61F 2/2403; A61F 2/2406
See application file for complete search history.

(56) References Cited

U.S. PATENT DOCUMENTS

| | | | | |
|---|---|---|---|---|
| 3,938,197 A | * | 2/1976 | Milo | A61F 2/2403 623/2.21 |
| 4,556,996 A | * | 12/1985 | Wallace | A61F 2/2412 623/2.2 |
| 2010/0023121 A1 | * | 1/2010 | Evdokimov | A61F 2/2403 623/2.1 |
| 2021/0212815 A1 | * | 7/2021 | Perrier | A61F 2/2418 |

\* cited by examiner

*Primary Examiner* — Suba Ganesan

(57) ABSTRACT

A prosthetic heart valve with a dihedral guard safety mechanism includes a base, three or more leaflets that extend from the base, hinges located at the connection between the base and each leaflet, allowing the leaflet to rotate, a dihedral guard that protrudes out from the inner edge of the base, and a dihedral guard slot on the bottom face of each leaflet that forms a flush connection with the dihedral guard safety mechanism when the prosthetic heart valve is in a closed position. The dihedral guard is set at a specified angle and lays under each leaflet, preventing the leaflets from falling to a position or angle lower than the dihedral guard when the valve is subject to negative pressure, in turn, mitigating a potential prosthetic heart valve failure.

3 Claims, 8 Drawing Sheets

PROSTHETIC HEART VALVE WITH A DIHEDRAL GUARD MECHANISM

CROSS-REFERENCE TO RELATED APPLICATIONS

This application claims priority to U.S. Provisional Application No. 63/233,384 entitled Prosthetic Heart Valve with a Dihedral Guard, filed Aug. 16, 2021, which is hereby incorporated by reference in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

FIELD OF INVENTION

The present invention relates generally to prosthetic heart valves and in particular to a prosthetic heart valve with safety mechanisms to prevent the failure of the prosthetic heart valve. This invention directs to a mechanical heart valve with a leaflet structure assembled on an annular base through a series of hinges, with protrusions to function as a dihedral guard, to prevent the leaflets from over rotation into an orientation opposite of intended flow direction of blood.

BACKGROUND OF INVENTION

Through the onset of detrimental heart valve complications, such as valve regurgitation and valve stenosis, patients may require a surgically implanted prosthetic heart valve. Prosthetic heart valves are medical devices that mimic the function of biological heart valves; prosthetic heart valves attempt to replicate the function of natural heart valves found in the body, enabling better patient health outcomes. Heart valve complications are typically classified into two distinct categories: regurgitation and stenosis. Regurgitation, or backflow, is diagnosed when a heart valve enables blood leakage back into the chambers rather than flowing forward through the heart or into an artery. Stenosis is diagnosed when the flaps of a heart valve thicken or stiffen, preventing the heart valve from fully opening, in turn, preventing sufficient blood flow. Prosthetic heart valves are typically separated into three broad classes: mechanical heart valves, bioprosthetic tissue valves, and engineered tissue valves. However, the most dominant categories of prosthetic heart valves largely consist of mechanical and bioprosthetic heart valves. Mechanical prosthetic heart valves are made of strong, durable metals and are generally considered the safest option. They almost always require the patient to use blood-thinning medicine to reduce the chance of blood clots. Bioprosthetic heart valves are heart valves taken from animals as well as, although rarely, from human donors and they may not require blood-thinning medications. However, current prosthetic heart valve options lack stable and effective safety mechanisms, enabling the onset of leaflet distortions, hinge fractures, poor valve longevity, and prosthetic valve leakages when the prosthetic valve is subject to unideal conditions, high volume blood flow, or high blood pressure.

Prior arts and devices used for the previous scenario do not effectively provide solutions to the above-mentioned problem. Much effort has been made to maximize specific functions of the safety mechanism in the present invention. This is seen heavily in the unique features of the various safety mechanism and embodiment of the present invention. The present invention's utility is evident in its disclosure. The invention serves to provide a prosthetic heart valve that would contain a safeguard against a detrimental orientation of the leaflets.

DESCRIPTION OF PRIOR ARTS

The U.S. Pat. No. 6,896,700 (Lu et al) discloses a trileaflet heart valve includes an annular valve base with an inner surface forming an orifice through which blood flows from the upstream side to the downstream side. Three protruding hinges, each with concave sockets on opposite sides, are formed on the inner surface. Each hinge has a downstream face and an upstream face connected by a ridge. Three leaflets are respectively arranged between adjacent hinges. Each leaflet has round pivots on both sides that rest inside the concave sockets, allowing the leaflets to freely rotate in the annular valve base. When the leaflets are subject to positive pressure from the blood flow, the leaflets are pushed open and allow a central flow. When the leaflets are subject to negative pressure, the leaflets are closed to occlude the blood flow.

The U.S. Pat. No. 10,182,907A (Lapeyre et al) discloses a mechanical prosthetic heart valve, which includes an annular support on which at least two movable flaps and several articular extensions are arranged in an articulated manner. Each flap includes a central part framed by two lateral wings that each cooperate with an articular extension by way of an end portion that has an articulation facet. The two articulation facets of each flap together make up a surface area of less than 5% of the total outer surface area of the flap.

The U.S. Pat. No. 9,339,381 (Johnson et al) discloses a prosthetic mitral heart valve having four separate flexible leaflets. The heart valve includes a support frame that may be non-circular, for example elliptical or "D-shaped". The support frame may have an undulating outflow edge defined by four inflow cusps and four outflow commissures to which each of the flexible leaflets attaches. The support frame may comprise an undulating wire form and a surrounding stent defining a structure having four cantilevered posts projecting in the outflow direction to support the four leaflets. The heart valve is designed to be secured in the annulus and function as a standalone unit without papillary muscle connections to the leaflets. The four leaflets may be arranged in two opposed pairs, one pair being smaller than the other pair. The larger pair of leaflets may be identical or differently sized. Existing sizes of heart valve leaflets may be utilized with the smaller leaflets being at least two leaflet sizes smaller than the larger leaflets in odd millimeter increments.

The U.S. Pat. No. 8,052,747 (Melnikov et al) discloses a heart valve prosthesis disclosed in two- and three-leaflet versions including a ring-shaped body, leaflets, and leaflet turn stops. For the two-leaflet version, the stops represent two pairs of prominences located on a body end surface facing the blood down-flow. The first pair has internal surfaces, at least partially made flat, adapted to interact with flat sections of the leaflets to restrict the return blood flow in the closed position. The first pair is equipped with at least two rests interacting with a leaflet top surface facing the blood down-flow in its open position determining a leaflet turning angle. Each prominence of the second pair is located opposite a portion of the lateral surface of the corresponding leaflet most distant from a leaflet central surface and can interact with its internal surface with that part of the lateral surface during the opening of the heart valve prosthesis.

The U.S. Pat. No. 6,991,649 (Sievers et al) discloses an artificial heart valve for the replacement of an aortic or a mitral valve, including an annular body, which is provided at its outer circumference with means for mounting the artificial valve in place by surgical procedures and which defines in its interior a blood flow passage in which valve flap elements are pivotally supported to open or close the blood flow passage depending on their pivot positions, the annular body includes circumferentially spaced projections extending into the flow passage and being provided at their inner ends with pivot joints on which the valve flap elements are pivotally supported.

The U.S. Pat. No. 11,224,506 (Amerio et al) discloses a mechanical prosthetic heart valve having a ring, multiple hinges, and multiple leaflets. The hinges are attached to the ring and are evenly spaced from one another along the inner circumference of the ring. Each leaflet is rotatably attached to a hinge by an opening located in the center of the lower portion of the leaflets. The ring can include multiple protrusions located along the inner circumference of the ring. The protrusions of the ring limit the opening angle of the leaflets. By limiting the opening angle of the leaflets, wear and tear of the hinges and leaflets, as well as the probability of malfunction of the mechanical prosthetic heart valve is reduced. In addition, limiting the opening angle of the leaflets may increase the opening and closing speed of the leaflets, thus improving the performance of the mechanical prosthetic heart valve when the patient is experiencing an elevated cardiac frequency.

The U.S. Pat. No. 6,645,244 (Shu et al) discloses an improved artificial mechanical heart valve prosthesis having an improved leaflet hinge mechanism which improves washing of the hinge recess, reduces leaflet closing impact force, and decreases noise and wear. A generally annular valve body having an annular interior surface extending between an inflow rim and an outflow rim thereof defines an annular orifice therethrough. A pair of leaflets are supported on said annular valve body for alternately blocking blood flow in an inflow direction when seated against the annular interior side wall in a closed position and then allowing the flow of blood through the said annular orifice in a predetermined blood outflow direction when rotated into an open position.

The present invention is similar to already existing prosthetic heart valves, but with a unique configuration. The main feature of the present invention disclosed herein is a prosthetic heart valve containing a dihedral guard mechanism which further acts as a barrier that prevents the leaflets from over-rotating from their intended position and, in turn, prevents valve leakages. Furthermore, the use of a physical rim or protrusion to support the bottom face of the leaflet helps to relieve stress, caused by high volume blood flow and pressure, from the hinges and leaflets, allowing for greater valve longevity. According to various aspects of the disclosure, the invention includes a base, numerous leaflets that extend from the base, a hinge located at the connection between the base and each leaflet, allowing the leaflet to rotate, a dihedral guard that protrudes inward from the inner edge of the base, and a dihedral guard slot on the bottom face of each leaflet.

BRIEF SUMMARY OF THE INVENTION

The following summary is provided to facilitate an understanding of some of the innovative features unique to the present invention, this is not intended to be a full description. A full description of the various aspects of the invention can be gained by taking the entire specification, claims, and abstract as a whole.

The present invention disclosed herein introduces a prosthetic heart valve containing a safety mechanism. According to various aspects of the disclosure, the invention includes a base, numerous leaflets that extend from the base, a hinge located at the connection between the base and each leaflet, allowing the leaflet to rotate, a dihedral guard that protrudes inward from the inner edge of the base, and a dihedral guard slot on the bottom face of each leaflet. The dihedral guard is set at a specified angle and lays under each leaflet and the dihedral guard slots on the leaflets allow the leaflet to form a flush connection with the dihedral guard when the valve is closed, preventing the leaflets from falling to a position or angle lower than the dihedral guard, in turn, mitigating a potential prosthetic heart valve failure.

DETAILED DESCRIPTION OF THE INVENTION

References in this description to "an embodiment", "one embodiment", or the like, mean that the particular feature, function, or characteristic being described is included in at least one embodiment of the present disclosure. Occurrences of such phrases in this description do not necessarily all refer to the same embodiment, nor are they necessarily mutually exclusive.

FIGS. 1, 2, 3, and 4 illustrate a prosthetic heart valve apparatus (100) according to one embodiment of the present disclosure.

Figure 1:
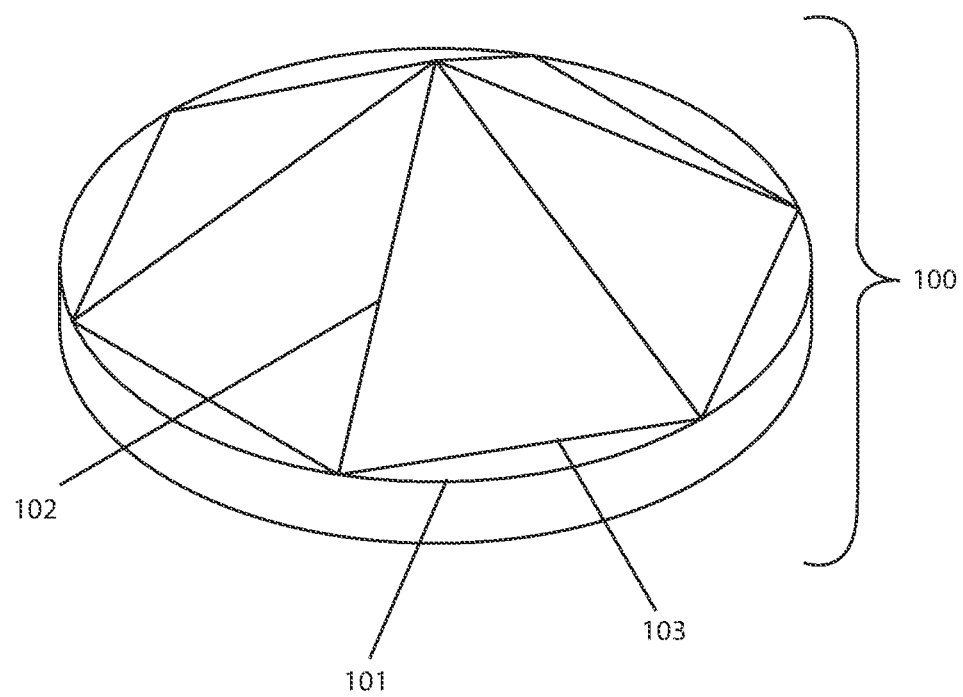
FIGS. 1 and 2 illustrate a prosthetic heart valve, in accordance with one embodiment of the disclosure, in a closed position

FIG. 1 is an isometric view of a prosthetic heart valve apparatus (100) in a closed position.

Figure 2:
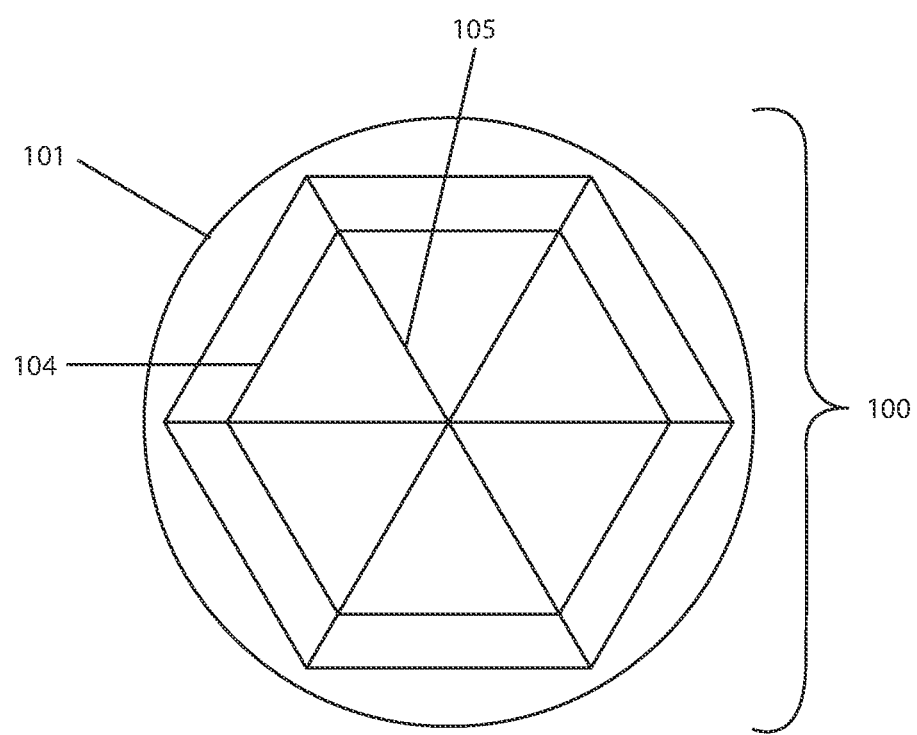

FIG. 2 is a bottom view of a prosthetic heart valve apparatus (100) in a closed position.

Figure 3:
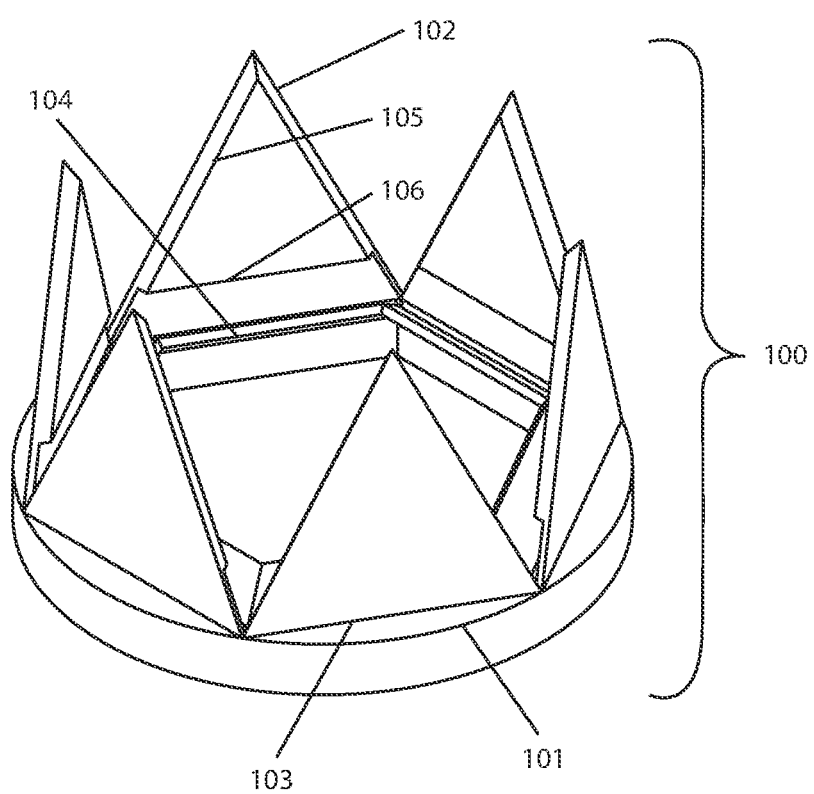
FIGS. 3 and 4 illustrate a prosthetic heart valve, in accordance with one embodiment of the disclosure, in an open position

FIG. 3 is an isometric view of a prosthetic heart valve apparatus (100) in an open position.

Figure 4:
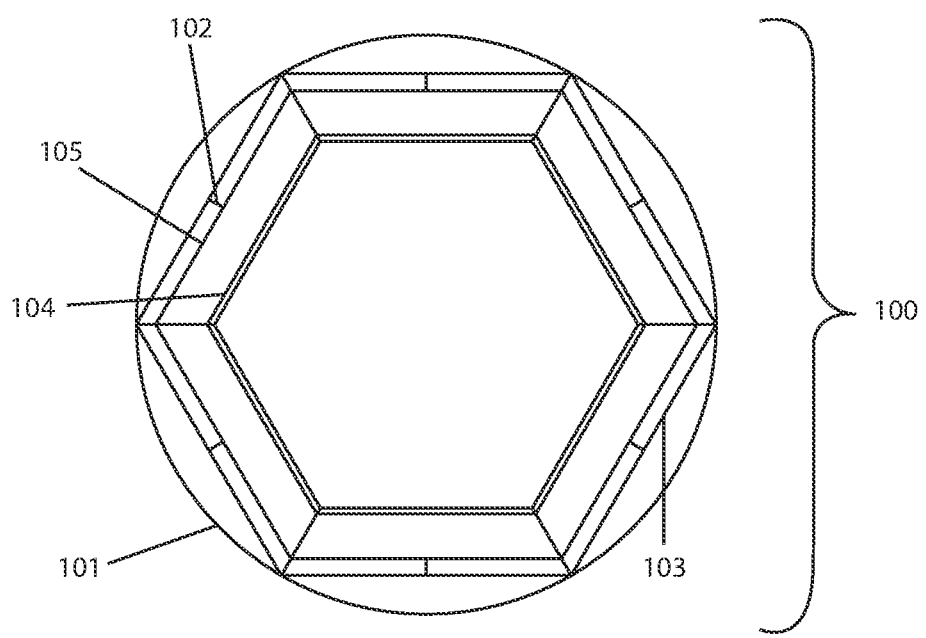

FIG. 4 is a top view of a prosthetic heart valve apparatus (100) in an open position. In one embodiment the prosthetic heart valve apparatus (100) contains an annular base (101), identical flat, triangular leaflets (102), a hinge (103), a dihedral guard (104), and a dihedral guard slot (106) located on the bottom face of each leaflet (105). The annular base (101) of the prosthetic heart valve apparatus (100) can be made from biological tissue, carbon, metal, plastic, 3D printing filament materials, or any other material as contemplated by a person having ordinary skill in the art. The annular base (101) contains an open cavity in its center that allows blood or other fluid to flow through. The annular base (101) serves as a secure foundation for the multiple flat, triangular leaflets (102) attached via a hinge (103) to simulate the opening and closing functions of a heart valve. In one embodiment of the present disclosure, the annular base (101) may be created from saturable materials that allow the annular base (101) to be directly sutured to its designated location in the heart. The flat, triangular leaflets (102) of the prosthetic heart valve apparatus (100) can be made from biological tissue, carbon, metal, plastic, 3D printing filament materials, or any other material as contemplated by a person having ordinary skill in the art. The flat, triangular leaflets (102) are constructed in a manner that when in a closed position, the flow of blood or other fluid is blocked by the leaflets (102). The leaflets (102) attach to the annular base (101) of the prosthetic heart valve apparatus (100) through a hinge (103). The hinge (103) allows the leaflets (102) to rotate about a horizontal axis relative to the annular base (101). In one embodiment, the hinge (103) may utilize a mechanical hinge mechanism to facilitate the rotating movement of the leaflets (102). In another embodiment, the hinge (103) may utilize a live hinge mechanism to facilitate the rotating movement of the leaflets (102). Each leaflet (102) contains a dihedral guard slot (106) on the bottom face of each leaflet (105). The bottom face of the leaflet (105) refers to the face of the leaflet closest to the center of the valve. The bottom face of the leaflet (105) is adjacent to the face connected to the hinge (103) and makes direct contact with the dihedral guard (104) when the valve is in the closed position. The dihedral guard slot (106) exists on the bottom face of each leaflet (105) with a size and depth large enough to facilitate a flush connection between the bottom face of the leaflet (105) and the dihedral guard (104) when the valve is in its closed position. The dihedral guard (104) of the prosthetic heart valve apparatus (100) can be made from biological tissue, carbon, metal, plastic, 3D printing filament materials, or any other material as contemplated by a person having ordinary skill in the art. The dihedral guard (104) is located on the inner edge of the annular base (101) and protrudes inward, towards the center of the cavity. The dihedral guard (104) protrudes upwards from the inner edge of the annular base (101) towards the center of the prosthetic valve apparatus (100) at an angle between 0 and 90 degrees relative to the top edge of the annular base (101). In one embodiment, the dihedral guard (104) is located under each individual leaflet (102) and forms a flush connection with each dihedral guard slot (106) on the bottom face of each leaflet (105) when the valve is in the closed position, preventing the leaflets (102) from falling to an angle or position lower than the dihedral guard (104) and preventing potential prosthetic valve failure. In one embodiment, the dihedral guards (104) under each leaflet are connected, forming a polygonal-like ring.

FIGS. 5, 6, 7, 8, illustrate a prosthetic heart valve apparatus (100) according to one embodiment of the present disclosure.

Figure 5:
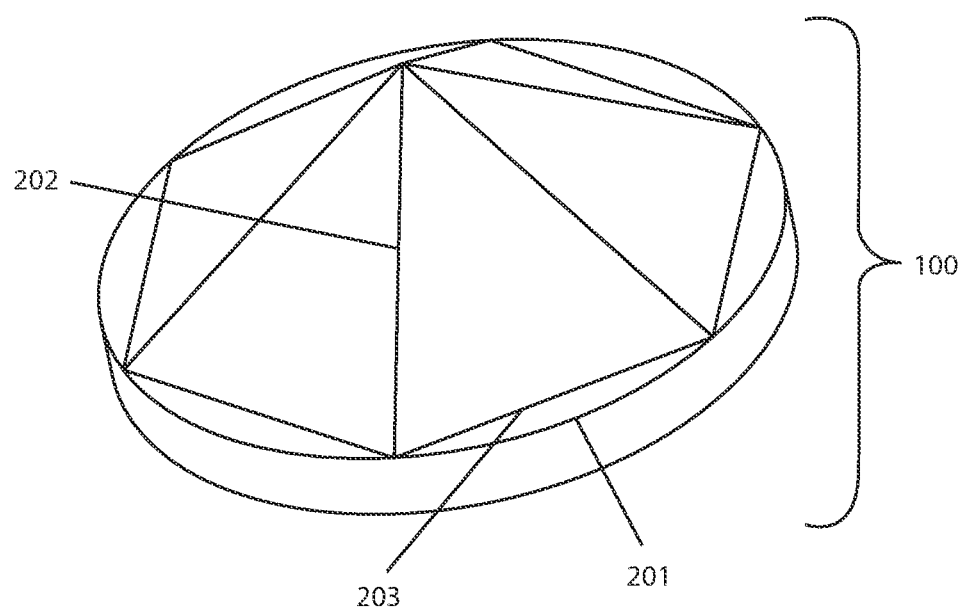
FIGS. 5 and 6 illustrate a prosthetic heart valve, in accordance with one embodiment of the disclosure, in a closed position

FIG. 5 is an isometric view of a prosthetic heart valve apparatus (100) in a closed position.

Figure 6:
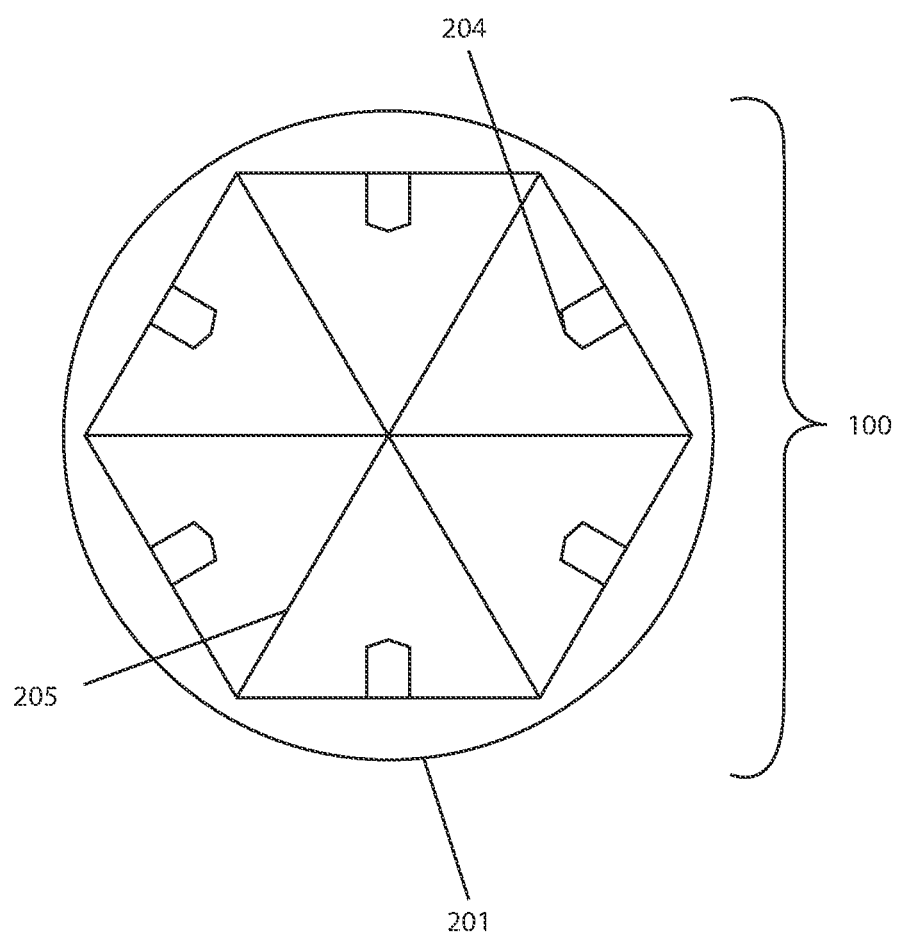

FIG. 6 is a bottom view of a prosthetic heart valve apparatus (100) in a closed position.

Figure 7:
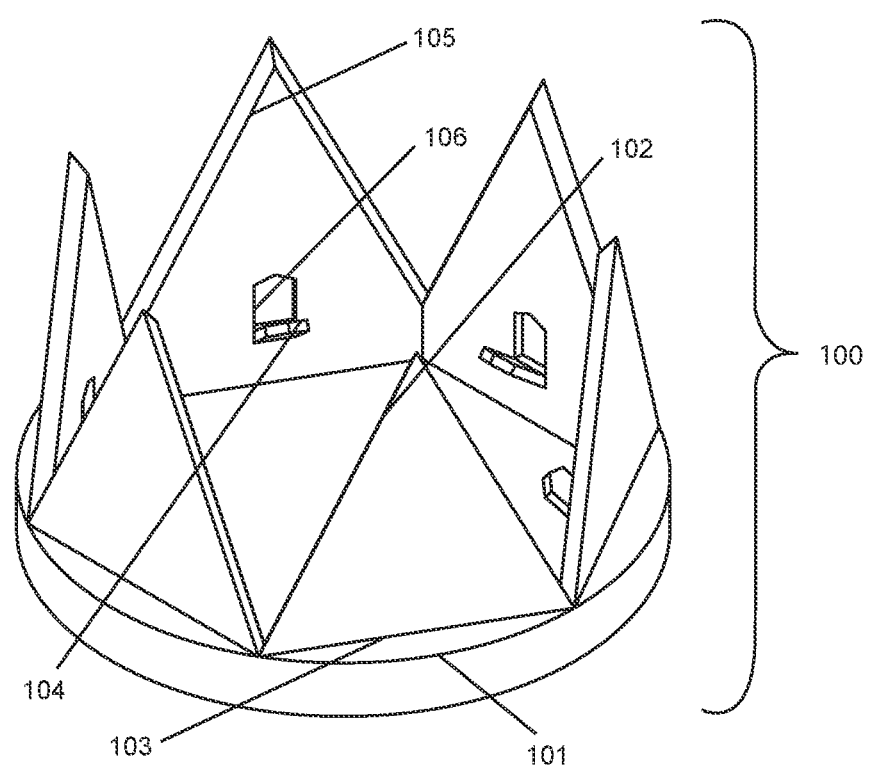
FIGS. 7 and 8 illustrate a prosthetic heart valve, in accordance with one embodiment of the disclosure, in an open position

FIG. 7 is an isometric view of a prosthetic heart valve apparatus (100) in an open position.

Figure 8:
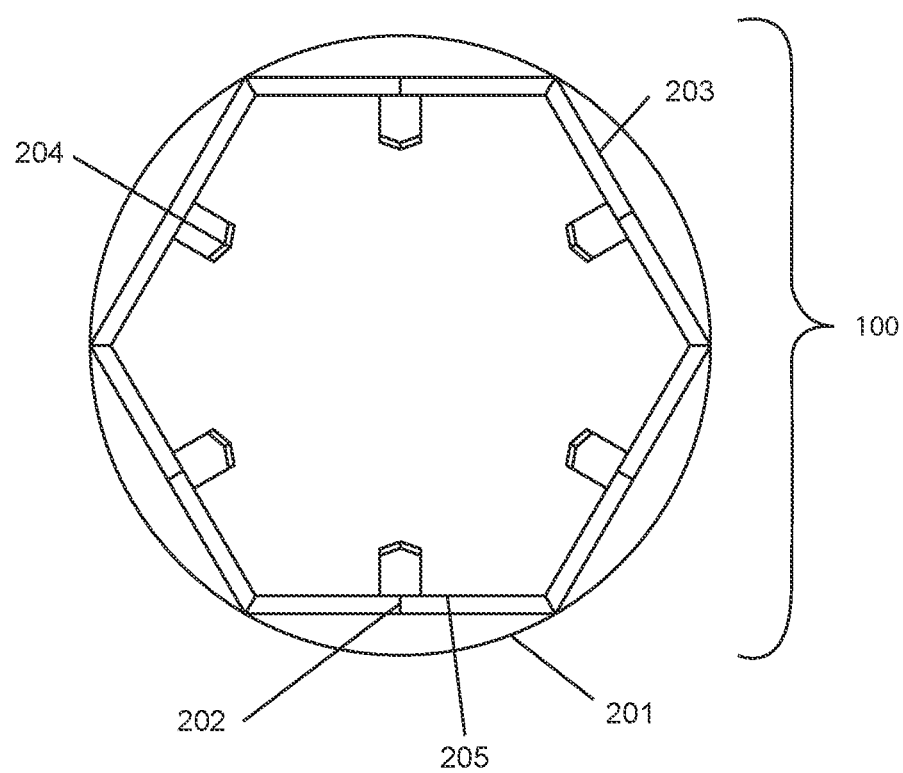

FIG. 8 is a top view of a prosthetic heart valve apparatus (100) in an open position. In one embodiment the prosthetic heart valve apparatus (100) contains an annular base (201), identical flat, triangular leaflets (202), a hinge (203), a dihedral guard (204), and a dihedral guard slot (206) located on the bottom face of each leaflet (205). The dihedral guard (204) of the prosthetic heart valve apparatus (100) is located on the inner edge of the annular base (201). In one embodiment, the dihedral guard (204) is located under each individual leaflet (202) and forms a flush connection with each dihedral guard slot (206) on the bottom face of each leaflet (205) when the valve is in the closed position, preventing the leaflets (202) from falling to an angle or position lower than the dihedral guard (204) and preventing potential prosthetic valve failure. In another embodiment, one individual dihedral guard (204) is located under each leaflet. In another embodiment, multiple dihedral guards (204) are located under each leaflet with multiple corresponding dihedral guard slots (206) on the bottom face of each leaflet (205).

What is claimed:

1. A prosthetic heart valve apparatus comprising of;
    a. An annular base with a cavity in its center that allows fluid to flow through it;
    b. Three or more identical flat, triangular leaflets that attach to the top of said annular base via a series of hinges;
    c. A series of hinges integrated into the annular base that attaches the leaflets to the base and allows the leaflets to rotate around a horizontal axis relative to the base;
    d. A dihedral guard slot on the bottom face of each leaflet with a size and depth large enough to form a flush connection with a dihedral guard that further protrudes from the annular base and resides under each leaflet;
    e. A dihedral guard that protrudes upward towards the leaflets and inward towards the center of the valve from the inner edge of the annular base at a set angle and forms a flush connection with each dihedral guard slot located on the bottom face of each triangular leaflet when the valve is in its closed position, preventing the leaflets from over rotation into an orientation opposite of the intended blood flow direction.

2. A prosthetic heart valve apparatus of claim 1) further comprising a dihedral guard that is separated into multiple identical protrusions, where an equal number of protrusions and corresponding dihedral guard slots are present under each leaflet.

3. A prosthetic heart valve apparatus of claim 1) further comprising the integration of magnets into the leaflets, dihedral guard slots, or dihedral guard that aid the formation of a flush connection between the dihedral guard and dihedral guard slots.

* * * * *